(12) United States Patent
Zorn et al.

(10) Patent No.: US 6,548,502 B2
(45) Date of Patent: Apr. 15, 2003

(54) DOPAMINE D4 LIGANDS FOR THE TREATMENT OF NOVELTY-SEEKING DISORDERS

(75) Inventors: Stevin H. Zorn, No. Stonington, CT (US); Mark A. Sanner, Old Saybrook, CT (US); Antor F. Fliri, Stonington, CT (US); Patricia A. Seymour, Westerly, RI (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/915,605

(22) Filed: Jul. 26, 2001

(65) Prior Publication Data

US 2002/0049209 A1 Apr. 25, 2002

Related U.S. Application Data

(60) Provisional application No. 60/221,268, filed on Jul. 27, 2000.

(51) Int. Cl.$^7$ ............................................. A61K 31/498
(52) U.S. Cl. ...................................................... 514/249
(58) Field of Search ........................................ 514/249

(56) References Cited

U.S. PATENT DOCUMENTS

| | | | | |
|---|---|---|---|---|
| 5,616,585 A | * | 4/1997 | Bright ........................ | 514/249 |
| 5,852,031 A | | 12/1998 | Desai et al. ................ | 514/279 |
| 5,916,914 A | | 6/1999 | Connor et al. .............. | 514/456 |
| 5,922,719 A | | 7/1999 | Johnson et al. ............. | 514/253 |
| 5,945,421 A | | 8/1999 | Belliotti et al. ............. | 514/253 |
| 5,968,478 A | | 10/1999 | Fu et al. ..................... | 424/1.81 |
| 5,976,497 A | | 11/1999 | Pollak et al. ............... | 424/1.85 |
| 5,998,414 A | | 12/1999 | Wang et al. ................. | 514/253 |
| 6,040,448 A | | 3/2000 | Greenlee et al. ............ | 544/363 |
| 6,051,605 A | | 4/2000 | Capiris et al. .............. | 514/523 |

FOREIGN PATENT DOCUMENTS

| | | |
|---|---|---|
| EP | 1074257 | 2/2001 |
| WO | 9610571 | 4/1996 |
| WO | WO 9909025 | 2/1999 |
| WO | WO 9943670 | 2/1999 |
| WO | WO 9921850 | 5/1999 |
| WO | WO 9923092 | 5/1999 |
| WO | WO 9940068 | 8/1999 |
| WO | WO 9947513 | 9/1999 |
| WO | WO 0020414 | 4/2000 |
| WO | WO 0012500 | 9/2000 |

OTHER PUBLICATIONS

Downey et al., J. Nervous and Mental Diseases, 187(1), pp 32–38, Jan. 1997.*

D. D. Dougherty, et al., Dopamine Transporter Density in Patients with Attention Deficit Hyperactivity Disorder, vol. 354(9196), Pp. 2132–2133, Dec. 18/25,( 1999).

N. A. Shapira, et al., Psychiatric Features of Individuals with Problematic Internet use, Elsevier, Journal of Affective Disorders, 57 (2000), Pp. 267–272.

P. F. Sullivan, et al., Novelty Seeking and a Dopamine Transporter Gene Polymorphism (DAT1), Brief Reports, Biol. Psychiatry (1997); 42:1070–1072.

D. C. Rowe, et al., Dopamine DRD4 Receptor Polymorphism and Attention Deficit Hyperactivity Disorder, Molecular Psychlatry (1998) 3, 419–426.

T. Roman, et al., Lack of Association of the Dopamine D4 Receptor Gene Polymorphism with Alcoholism in a Brazilain Population, Addiction Biology (1999) 4, 203–207.

J. Gelernter, et al., D4 Dopamine–Receptor (DRD4) Alleles and Novelty Seeking in Substance–Dependent, Personality–Disorder, and Control Subjects, Am. J. Hum. Genet. 61:1144–1152, 1997.

C. H. D. Bau, et al., Dopamine D4 Receptor Gene and Personality Dimensions in Brazilian Male Alcoholics, Psychiartic Genetics 1999; 9:139–143.

J. Ekelund, et al., The Dopamine D4 Receptor Gene and Novelty Seeking, Am. J. Psychiartry 157:11, Nov. 2000.

J. Ihome, et al., Dopamine D3 Receptor Gene Polymorphism and Alcohol Dependence: Relation to Personality Rating, Psychiatric Genetics 1999; 9:17–21.

G. A. Wiesbeck, et al., Neuroendocrine Support for a Relationship between "Novelty Seeking" and Dopaminergic Function in Alcohol–Dependent Men, Pergamon, Psychoneuroendorinology, vol. 20, No. 7, pp. 755–761, 1995.

* cited by examiner

*Primary Examiner*—Phyllis G. Spivack
(74) *Attorney, Agent, or Firm*—P. C. Richardson; P. H. Ginsburg; A. D. Joran

(57) ABSTRACT

The present invention provides a method of treating or preventing a novelty-seeking disorder, such as pathological gambling, attention deficit disorder with hyperactivity disorder and sex addiction, comprising administering a compound which is a dopamine D4 receptor ligand, or a pharmaceutically acceptable salt thereof.

3 Claims, No Drawings

DOPAMINE D4 LIGANDS FOR THE TREATMENT OF NOVELTY-SEEKING DISORDERS

This application claims the benefit of U.S. Provisional Application Serial No. 60/221,268, filed Jul. 27, 2000.

The present invention relates to a method of treating or preventing a novelty-seeking disorder selected from pathological gambling, attention deficit disorder with hyperactivity disorder, substance addiction, such as drug addiction and alcohol addiction, and sex addiction, using a dopamine D4 ligand. It also relates to a method of treating or preventing such disorders in mammals by administering a pyrido[1,2a] pyrazine derivative, benzimidazole derivative, bicyclic compound, spirocyclic benzo furan derivative, indole derivative or a related compound that is a dopamine D4 receptor ligand.

It has been determined that dopamine D4 receptors are related to various behavioral and personality disorders including novelty seeking disorders (See, e.g., Tarazi et al., *Mol. Psychiatry*, 4, 529–538(1999). The trait of novelty seeking was found to be related to dopaminergic activity in alcoholic men (Wiesbeck et al., *Psychoneuroendocrinology*, 20, 7(1999)). A large Finnish study provides support for an association between the D4 receptor gene (DRD4) and the behavioral trait of novelty seeking (Ekelund et al., *Am. J. Psychiatry*, 156, 1453–5 (1999)). Recent evidence has accumulated which supports a clinical linkage between attention deficit disorder with hyperactivity disorder, which has been associated with the novelty seeking trait, and dopamine receptor expression (see, e.g., Tarazi et al., supra; Anderson et al., *Neuroscience & Biobehavioral Rev.*, 24, 137–41 (2000)) and dopamine transporter gene expression (see, e.g., Dougherty et al., *The Lancet*, 354, 2132–2133 (1999)). Further evidence has been found for an association between the D4 gene and a susceptibility to pathological gambling (Comings, *CNS Spectr.*, 3, 20–37 (1998)) and a susceptibility to opioid addiction and substance abuse (Kotler et al., *Mol. Psychiatry*, 2, 251–254 (1997)).

The following references refer, collectively, to pyrido[1,2a]pyrazine derivatives, benzimidazole derivatives, bicyclic compounds, spirocyclic benzofuran derivatives, indole derivatives or related compounds that exhibit activity as dopamine D4 receptor ligands: U.S. Pat. No. 5,852,031, issued on Dec. 22, 1998; U.S. Pat. No. 5,883,094, issued on Mar. 16, 1999; U.S. Pat. No. 5,889,010, issued on Mar. 30, 1999; PCT International Application PCT/IB97/00978, published as WO98/08835 on Mar. 5, 1998; U.S. patent application Ser. No. 5,877,317 issued on Mar. 2, 1999; U.S. patent application Ser. No. 5,021,420, issued on Jun. 4, 1991; U.S. patent application Ser. No. 5,633,376, issued on May 27, 1997; U.S. patent application, Ser. No. 5,432,177, issued on Nov. 9, 1994; U.S. patent application Ser. No. 5,622,950, issued on Apr. 22, 1997, PCT International Application No. PCT/EP93/01438, published as WO94/00458 on Jan. 6, 1994; PCT International Application No. PCT/IB98/01198, published as WO99/09025 on Feb. 25, 1999; U.S. patent application Ser. No. 5,998,414, issued on Dec. 7, 1999; U.S. patent application Ser. No. 5,968,478, issued on Oct. 19, 1999; U.s. patent application Ser. No. 6,040,448, issued on Mar. 21, 2000; U.S. patent application Ser. No. 6,051,605, issued on Apr. 18, 2000; U.S. patent application Ser. No. 5,945,421, issued on Aug. 31, 1999; and U.S. patent application Ser. No. 5,798,350, issued on Aug. 25, 1998. All of the foregoing PCT International Applications designate the United States. The foregoing patents and patent applications are incorporated by reference in their entirety.

SUMMARY OF THE INVENTION

This invention relates to a method of treating or preventing a novelty-seeking disorder selected from pathological gambling, attention deficit disorder with hyperactivity disorder (ADHD), substance addiction (e.g., drug addiction and alcohol addiction) and sex addiction in a subject, including a human, comprising administering to the subject an effective amount of:

(a) a compound of formula I:

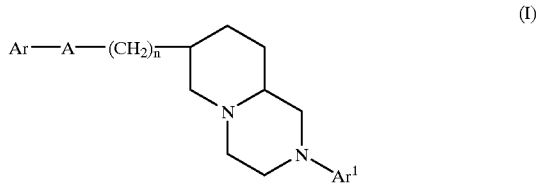

wherein Ar is phenyl, naphthyl, benzoxazolonyl, indolyl, indolonyl, benzimidazolyl, quinolyl, furyl, benzofuryl, thienyl, benzothienyl, oxazolyl, or benzoxazolyl;

$Ar^1$ is phenyl, pyridinyl, pyridazinyl, pyrimidinyl, pyrazinyl, benzisoxazolyl, or benzisothiazolyl; A is O, S, SO, $SO_2$, C=O, CHOH, or —($CR^3R^4$)—; n is 0, 1 or 2; each of Ar and $Ar^1$ may be independently and optionally substituted with one to four substituents independently selected from the group consisting of fluoro, chloro, bromo, iodo, cyano, nitro, thiocyano, —SR, —SOR, —$SO_2R$, —$NHSO_2R$, —(C1–C6)alkoxy, —$NR^1R^2$, —$NRCOR^1$, —$CONR^1R^2$, Ph, —COR, COOR, —($C_1$–$C_6$)alkyl, —($C_1$–$C_6$)alkyl substituted with one to six halogens, —($C_3$–$C_6$)cycloalkyl, and trifluoromethoxy;

each and every R, $R^1$, and $R^2$ is independently selected from the group consisting of hydrogen, —($C_1$–$C_6$) alkyl, —($C_1$–$C_6$)alkyl substituted with one to thirteen halogens selected from fluorine, chlorine, bromine and iodine, phenyl, benzyl, —($C_2$–$C_6$)alkenyl, —($C_3$–$C_6$)cycloalkyl, and —($C_1$–$C_6$)alkoxy;

each and every $R^3$ and $R^4$ is independently selected from the group consisting of hydrogen, methyl, ethyl, n-propyl, or i-propyl; diastereomeric and optical isomers thereof; and pharmaceutically acceptable salts thereof;

(b) a compound of formula II:

II:

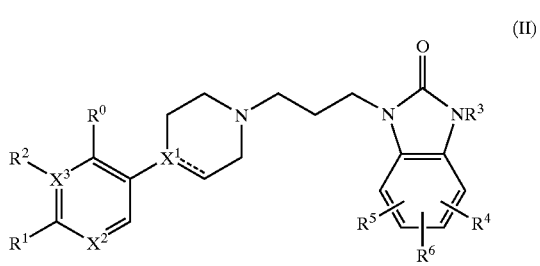

wherein $X^1$, $X^2$ and $X^3$ are independently selected from carbon and nitrogen;

$R^0$, $R^1$ and $R^2$ are independently selected from hydrogen, halo (e.g., chloro, fluoro, bromo or iodo), ($C_1$–$C_6$)alkyl optionally substituted with from one to three fluorine atoms and ($C_1$–$C_6$)alkoxy optionally substituted with from one to three fluorine atoms;

R³ is hydrogen, (C₁–C₆)alkyl or benzyl, wherein the phenyl moiety of said benzyl group may optionally be substituted with from one or more substituents, preferably with from zero to three substituents, independently selected from halo (e.g., chloro, fluoro, bromo or iodo), cyano, (C₁–C₆)alkyl optionally substituted with from one to three fluorine atoms, (C₁–C₆)alkoxy optionally substituted with from one to three fluorine atoms, (C₁–C₆)alkylsulfonyl, (C₁–C₆)alkylamino, amino, di—(C₁–C₆)alkylamino and (C₁–C₆)carboxamido;

R⁴, R⁵ and R⁶ are independently selected from hydrogen, halo (e.g., chloro, fluoro, bromo or iodo), cyano, (C₁–C₆)alkyl optionally substituted with from one to three fluorine atoms, (C₁–C₆)alkoxy optionally substituted with from one to three fluorine atoms, (C₁–C₆)alkylsulfonyl, (C₁–C₆)acylamino, (phenyl)[(C₁–C₆)acyl]amino, amino, (C₁–C₆)alkylamino and di-(C₁–C₆)alkylamino;

with the proviso that when X³ is nitrogen, R² is absent;

(c) a compound of formula III:

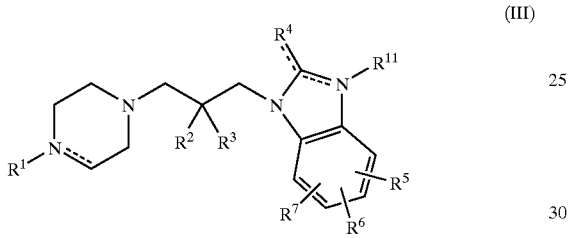

(III)

wherein each of the dotted lines represents an optional double bond;

X is carbon or nitrogen;

R¹ is benzyl, aryl selected from phenyl, indanyl and naphthyl, or heteroaryl selected from pyridyl, thienyl, furyl, thiazolyl, isothiazolyl, oxazolyl, isoxazolyl, triazolyl, quinolyl and imidazolyl, wherein each of the foregoing aryl, heteroaryl and (C₁–C₄)alkyl groups, and the phenyl moiety of the benzyl group, may optionally be substituted with one or more substituents, preferably with from zero to two substituents, independently selected from halo (e.g., chloro, fluoro, bromo or iodo), (C₁–C₆)alkyl optionally substituted with from one to three fluorine atoms, (C₁–C₆)alkoxy optionally substituted with from one to three fluorine atoms, cyano, —C(=O)R⁸, aryl and heteroaryl, wherein said aryl is selected from phenyl, indanyl and naphthyl and said heteroaryl is selected from pyridyl, thienyl, fiuyl, thiazolyl, isothiazolyl, oxazolyl, isoxazolyl, triazolyl, quinolyl and imidazolyl;

R² and R³ are independently selected from hydrogen, hydroxy, (C₁–C₆)alkyl, (C₁–C₆)alkoxy, cyano, —CONH₂ and —NHC(=O)R⁹, or R² and R³ together form an oxo group;

R⁴ is hydrogen, sulfur, oxygen, (C₁–C₆)alkyl, amino, —NHR¹⁰, —SR¹⁰, OR¹⁰ or hydroxy;

R⁵, R⁶ and R⁷ are independently selected from hydrogen, halo (e.g., chloro, fluoro, bromo or iodo), cyano, (C₁–C₆)alkyl optionally substituted with from one to three fluorine atoms, (C₁–C₆)alkoxy optionally substituted with from one to three fluorine atoms, (C₁–C₆)alkylsulfonyl, (C₁–C₆)acylamino, (phenyl)[(C₁–C₆)acyl]amino, amino, (C₁–C₆)alkylamino, di-(C₁–C₆)alkylamino, aryl and heteroaryl, wherein said aryl is selected from phenyl, naphthyl and indanyl, and said heteroaryl is selected from pyridyl, thienyl, furyl, thiazolyl, isothiazolyl, oxazolyl, isoxazolyl, triazolyl, quinolyl and imidazolyl;

R⁸, R⁹ and R₁₀ are independently selected from hydrogen and (C₁–C₆)alkyl; and

R¹¹ is hydrogen, (C₁–C₆)alkyl or benzyl, wherein the phenyl moiety of said benzyl may optionally be substituted with one or more substituents, preferably with from zero to two substituents, independently selected from halo (e.g., fluoro, chloro, bromo, or iodo), (C₁–C₆)alkyl optionally substituted with from one to three fluorine atoms, (C₁–C₆)alkoxy optionally substituted with from one to three fluorine atoms, amino, cyano, (C₁–C₆)alkylamino and di—(C₁–C₆)alkylamino;

with the proviso that: (a) R⁴ can not be either oxygen or hydroxy when both R² and R³ are hydrogen; (b) when the five membered ring of formula I contains a double bond, R¹¹ is absent; (c) when R⁴ is sulfur or oxygen, R⁴ is double bonded to the carbon to which is attached and such carbon is single bonded to both adjacent ring nitrogen atoms; and (d) when X is nitrogen and is double bonded to an adjacent carbon, R¹ is absent;

(d) a compound of formula IV:

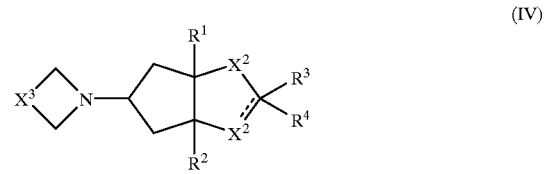

(IV)

and to pharmaceutically acceptable salts and solvates thereof wherein:

the dashed line in the above formula represents an optional double bond where X² is not O;

X¹ and X² are each independently selected from O and —(CH₂)ⱼ— wherein j is 1 or 2;

X³ is —CH(R⁵)N(R⁸)CH(R⁶)—, —CH(R⁵)C(R⁸)(R⁹)CH(R⁶)—, —C(R⁵)=C(R⁸)CH(R⁶)—, or —CH(R⁵)C(R⁸)=C(R⁶)—;

R¹ and R² are each independently H, hydroxy, or C₁–C₆ alkyl;

or R¹ and R² are taken together as a bond;

each R³ is independently selected from —S(O)ⱼR⁷ wherein j is an integer ranging from 0 to 2, —C(O)R⁷, —OR⁷, —NC(O)R⁷, —NR⁷R¹², and the substituents provided in the definition of R⁷ other than H;

R⁴ is absent where the dashed line in the above formula 1 represents a double bond or R⁴ is selected from H and the substituents provided in the definition of R³;

or R³ and R⁴ are taken together with the carbon atom to which each is attached to form a 5–10 membered mono-cyclic or bicyclic group wherein said cyclic group may be carbocyclic or heterocyclic with 1 to 3 heteroatoms selected from O, S, and —N(R¹¹)— with the proviso that two O atoms, two S atoms, or an O and S atom are not attached directly to each other; said cyclic group is saturated or partially unsaturated; aromatic or non-aromatic; 1 or 2 of the carbon atoms in said cyclic group optionally may be replaced by an oxo —C(O)— moiety; and said cyclic group is optionally substituted by 1 to 3 R¹⁰ groups;

$R^5$ and $R^6$ are each independently selected from H and $C_1-C_4$ alkyl;

or $R^5$ and $R^6$ are taken together as $-(CH_2)_q-$ wherein q is 2 or 3;

or $R^5$ or $R^6$ is taken together with $R^8$ as defined below;

each $R^7$ is independently selected from H, $-(CH_2)_t$($C_6-C_{10}$ aryl) and $-(CH_2)_t$(4–10 membered heterocyclic), wherein t is an integer ranging from 0 to 5; 1 or 2 of the carbon atoms of said heterocyclic group optionally may be replaced with an oxo $-C(O)-$ group; said aryl and heterocyclic $R^7$ groups are optionally fused to a benzene ring, a $C_5-C_8$ saturated cyclic group, or a 4–10 membered heterocyclic group; the $-(CH_2)_t-$ moieties of the foregoing $R^7$ groups optionally include a carbon-carbon double or triple bond where t is an integer between 2 and 5; and the foregoing $R^7$ groups, except H, are optionally substituted by 1 to 5 $R^{10}$ groups;

$R^8$ is selected from the substituents provided in the definition of $R^7$ other than H;

$R^9$ is selected from the substituents provided in the definition of $R^7$;

or $R^8$ and $R^9$ are taken together with the carbon to which each is attached to form a 5–10 membered mono-cyclic or bicyclic group wherein said cyclic group is carbocyclic or heterocyclic with 1 to 3 heteroatoms selected from O, S, and $-N(R^{11})-$ with the proviso that two O atoms, two S atoms, or an O and S atom are not attached directly to each other; saturated or partially unsaturated; aromatic or non-aromatic; 1 or 2 of the carbon atoms in said cyclic group optionally may be replaced by an oxo $-C(O)-$ moiety; and said cyclic group is optionally substituted by 1 to 3 $R^{10}$ groups;

or $R^8$ taken together with either $R^5$ or $R^6$ and the separate carbon atoms to which each is attached to form a fused 5–10 membered mono-cyclic or bicyclic group wherein said cyclic group may be carbocyclic or heterocyclic with 1 to 3 heteroatoms selected from O, S, and $-N(R^{11})-$ with the proviso that two O atoms, two S atoms, or an O and S atom are not attached directly to each other; saturated or partially unsaturated; aromatic or non-aromatic; 1 or 2 of the carbon atoms in said cyclic group optionally may be replaced by an oxo $-C(O)-$ moiety; and said cyclic group is optionally substituted by 1 to 3 $R^{10}$ groups;

each $R^{10}$ is independently selected from $C_1-C_{10}$ alkyl, $C_2-C_{10}$ alkenyl, $C_2-C_{10}$ alkynyl, halo, cyano, nitro, trifluoromethyl, trifluoromethoxy, azido, $-R^{11}$, $-C(O)R^{11}$, $-C(O)OR^{11}$, $-NR^{12}C(O)OR^{11}$, $-OC(O)R^{11}$, $-NR^{12}SO_2R^{11}$, $-SO_2NR^{11}R^{12}$, $-NR^{12}C(O)R^{11}$, $-C(O)NR^{11}$, $-NR^{11}R^{12}$, $-S(O)_j(C_1-C_6$ alkyl) wherein j is an integer ranging from 0 to 2, $-(CH_2)_m(C_6-C_{10}$ aryl), $-SO_2(CH_2)_m(C_6-C_{10}$ aryl), $-S(CH_2)_m(C_6-C_{10}$ aryl), $-O(CH_2)_m(C_6-C_{10}$ aryl) and $-(CH_2)_m$(4–10 membered heterocyclic), wherein m is an integer ranging from 0 to 4; said $C_1-C_{10}$ alkyl group optionally contains 1 or 2 hetero moieties selected from O, S and $-N(R^{12})-$ with the proviso that two O atoms, two S atoms, or an O and S atom are not attached directly to each other; said aryl and heterocyclic $R^{10}$ groups are optionally fused to a $C_6-C_{10}$ aryl group, a $C_5-C_8$ saturated cyclic group, or a 4–10 membered heterocyclic group; and said alkyl, aryl and heterocyclic $R^{10}$ groups are optionally substituted by 1 to 3 substituents independently selected from halo, cyano, nitro, trifluoromethyl, trifluoromethoxy, azido, $-NR^{12}SO_2R^{11}$, $-SO_2NR^{11}R^{12}$, $-C(O)R^{11}$, $-C(O)OR^{11}$, $-OC(O)R^{11}$, $-NR^{12}C(O)R^{11}$, $-C(O)NR^{11}R^{12}$, $-NR^{11}R^{12}$, $C_1-C_6$ alkyl, $-OR^{11}$ and the substituents listed in the definition of $R^{11}$;

each $R^{11}$ is independently selected from H, $C_1-C_{10}$ alkyl, $-(CH_2)_m(C_6-C_{10}$ aryl), and $-(CH_2)_m$(4–10 membered heterocyclic), wherein m is an integer ranging from 0 to 4; said alkyl group optionally includes 1 or 2 hetero moieties selected from O, S and $-N(R^{12})-$ with the proviso that two O atoms, two S atoms, or an O and S atom are not attached directly to each other; said aryl and heterocyclic $R^{11}$ groups are optionally fused to a $C_6-C_{10}$ aryl group, a $C_5-C_8$ saturated cyclic group, or a 4–10 membered heterocyclic group; and the foregoing $R^{11}$ subsituents, except H, are optionally substituted by 1 to 3 substituents independently selected from halo, cyano, nitro, trifluoromethyl, trifluoromethoxy, azido, $-C(O)R^{12}$, $-C(O)OR^{12}$, $-CO(O)R^{12}$, $-NR^{12}C(O)R^{13}$, $-C(O)NR^{12}R^3$, $-NR^{12}R^{13}$, hydroxy, $C_1-C_6$ alkyl, and $C_1-C_6$ alkoxy; and, each $R^{12}$ and $R^{13}$ is independently H or $C_1-C_6$ alkyl;

(e) a compound of formula V:

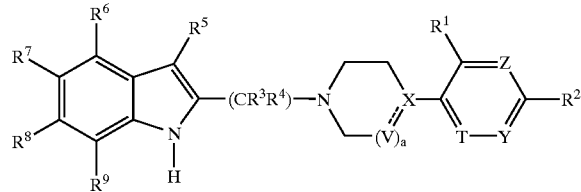

(V)

or the pharmaceutically acceptable salt thereof, wherein the broken line represents an optional double bond;

a is 0 or 1, wherein when a is 0, X may form an optional double bond with the carbon adjacent to V;

V is $CHR^{10}$ wherein $R^{10}$ is hydrogen or $(C_1-C_6)$alkyl;

T is nitrogen or CH;

X is nitrogen or $CR^{11}$ wherein $R^{11}$ is hydrogen, $(C_1-C_6)$alkyl, $(C_1-C_6)$alkoxy, hydroxy or cyano;

Y and Z are each independently nitrogen or $CR^{12}$ wherein $R^{12}$ is hydrogen, chloro, bromo, trifluoromethyl, trifluoromethoxy, cyano, $(C_1-C_6)$ alkoxy or $(C_1-C_6)$alkyl;

$R^1$ is hydrogen, fluoro, chloro, bromo, trifluoromethyl, trifluoromethoxy, cyano or $(C_1-C_6)$alkyl;

$R^2$, $R^6$, $R^7$, $R^8$ and $R^9$ are each independently selected from hydrogen, fluoro, chloro, bromo, trifluoromethyl, trifluoromethoxy, cyano, $(C_1-C_6)$ alkoxy and $(C_1-C_6)$alkyl;

$R^3$ and $R^4$ are each independently hydrogen or $(C_1-C_6)$ alkyl; and $R^5$ is hydrogen, $(C_1-C_6)$alkoxy, trifluoromethyl, cyano, $(C_1-C_6)$alkyl or $R^{13}CO-$ wherein $R^{13}$ is amino, $(C_1-C_6)$alkylamino, $((C_1-C_6)$alkyl$)_2$amino, $(C_1-C_6)$ alkyl, $(C_6-C_{10})$aryl;

or when a is 1, $R^1$ and $R^{10}$ may be taken together with the carbons to which they are attached to form a compound of the formula

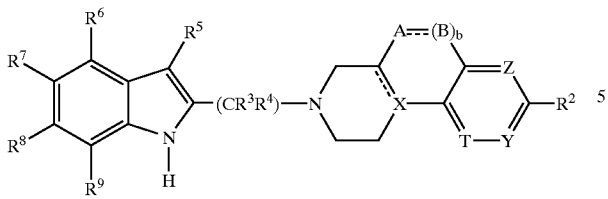

wherein the broken lines represent optional bonds; T, X, Y, Z, $R^2$, $R^3$, $R^4$, $R^5$, $R^6$, $R^7$, $R^8$ and $R^9$ are defined as above;
b is 0 or 1; and
A and B are each independently CH, $CH_2$, oxygen, sulfur, NH or nitrogen;
with the proviso that when X is nitrogen, the optional double bond between X and V does not exist;
with the proviso that when b is 0, the optional double bond between A and B does not exist; and with the proviso that when b is 1, A and B cannot both be oxygen or sulfur;

or (f) a compound of formula VI:

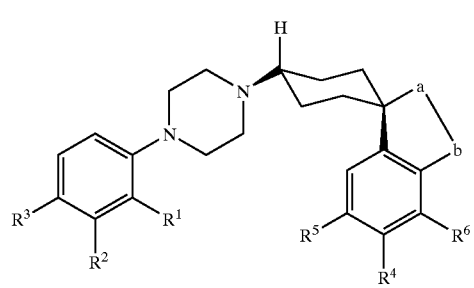

wherein a is oxygen, $CH_2$, $C(CH_3)_2$, $NR^{10}$, sulfur, SO or $SO_2$;
b is oxygen, $CH_2$, C=O, C=$NR^{11}$, C=NOH, $SO_2$, sulfur, SO, C=NO($C_1$–$C_5$)alkyl or $CR^7R^8$;
each of $R^1$ through $R^8$ is selected, independently, from hydrogen, halogen (e.g., chloro, fluoro, bromo or iodo), trifluoromethyl, cyano and hydroxy, or $R^7$ and $R^8$ together can be C(=O)$NH_2$ or C(=O)N($C_1$–$C_4$) alkyl, with the proviso that neither $R^7$ nor $R^8$ can be halo when a is oxygen, $NR^{11}$, sulfur, SO or $SO_2$; and
each of $R^{10}$ and $R^{11}$ is selected, independently, from hydrogen, benzyl and ($C_1$–$C_6$)alkyl;
and the pharmaceutically acceptable salts of such compounds.

The term "one or more substituents", as used herein, includes from one to the maximum number of substituents possible based on the number of available bonding sites.

The term "alkyl", as used herein, unless otherwise indicated, includes saturated monovalent hydrocarbon radicals having straight, branched or cyclic moieties or combinations thereof.

The term "alkoxy", as used herein, unless otherwise indicated, refers to radicals having the formula —O-alkyl, wherein "alkyl" is defined as above.

In one embodiment this invention relates to a method of treating or preventing a novelty-seeking disorder, comprising administering to the subject an effective amount of a compound of formula I wherein
Ar is phenyl, naphthyl, benzoxazolonyl, indolyl, indolonyl, benzimidazolyl, or quinolyl; $Ar^1$ is phenyl, pyridinyl, pyridazinyl, pyrimidinyl, pyrazinyl, or benzisoxazolyl; A is O, S, $SO_2$, C=O, CHOH, or $CH_2$; n is 0 or 1, wherein Ar and $Ar^1$ may be independently substituted with up to three substituents independently selected from the group consisting of fluoro, chloro, cyano, —$NR^1R^2$, —($C_1$–$C_6$)alkoxy, —COOR, —CONR$^1$R$^2$, and —($C_1$–$C_6$)alkyl and the pharmaceutically acceptable salts thereof.

Embodiments of Formula I

In certain embodiments, this invention relates to a method of treating or preventing a novelty-seeking, comprising administering to the subject an effective amount of a compound of formula I wherein A is O or S; n is 1; Ar is phenyl or substituted phenyl, and the pharmaceutically acceptable salts thereof.

In other embodiments, this invention relates to a method of treating or preventing a novelty-seeking disorder, comprising administering to the subject an effective amount of a compound of formula I wherein A is $CH_2$; n is 0; Ar is benzoxazolonyl or substituted benzoxazolonyl; and the pharmaceutically acceptable salts thereof.; or wherein A is $CH_2$; n is 0; Ar is indolyl or substituted indolyl; and the pharmaceutically acceptable salts thereof; or wherein A is C=O or CHOH; n is 0 or 1; Ar is phenyl or substituted phenyl; and the pharmaceutically acceptable salt thereof; or wherein A is O; Ar is fluorophenyl, difluorophenyl or cyanophenyl; $Ar^1$ is chloropyridinyl; and the pharmaceutically acceptable salt thereof; or wherein A is O; Ar is fluorophenyl, difluorophenyl or cyanophenyl; $Ar^1$ is fluoropyrimidinyl; and the pharmaceutically acceptable salt thereof; or wherein A is O; Ar is fluorophenyl, difluorophenyl or cyanophenyl; $Ar^1$ is fluorophenyl; and the pharmaceutically acceptable salt thereof; or wherein $Ar^1$ is 5-chloro-pyridin-2-yl; and the pharmaceutically acceptable salt thereof; or wherein $Ar^1$ is 5-fluoro-pyrimidin-2-yl; and the pharmaceutically acceptable salts thereof.

In preferred embodiments of the method, A is O; S, SO, or $SO_2$; C=O or CHOH; $CH_2$; phenyl or substituted phenyl;

In other preferred embodiments of the method, Ar is naphthyl or substituted naphthyl; benzoxazolonyl or substituted benzoxazolonyl; indolyl or substituted indolyl; indolonyl or substituted indolonyl; benzimidazolyl or substituted benzimidazolyl; quinolyl or substituted quinolyl.

In other preferred embodiments of the method, $Ar^1$ is phenyl or substituted phenyl; pyridinyl or substituted pyridinyl; pyridazinyl or substituted pyridazinyl; pyrimidinyl or substituted pyrimidinyl; pyrazinyl or substituted pyrazinyl; benzisoxazolyl or substituted benzisoxazolyl.

Specific preferred embodiments of the invention relate to a method of treating or preventing a novelty-seeking disorder, comprising administering to the subject an effective amount of the following compounds:

(7R,9aS)-7-(4-fluorophenoxy)methyl-2-(5-chloro-pyridin-2-yl)-2,3,4,6,7,8,9,9a-octahydro-1H-pyrido[1,2-a]pyrazine;

(7R,9aS)-7-(3,5-difluorophenoxy)methyl-2-(5-chloro-pyridin-2-yl)-2,3,4,6,7,8,9,9a-octahydro-1H-pyrido[1,2-a]pyrazine;

3-[(7R,9aS)-2-(5-chloro-pyridin-2-yl)-2,3,4,6,7,8,9,9a-octahydro-1H-pyrido[1,2-a]pyrazin-7-ylmethyl]-3H-benzoxazol-2-one;

3-[(7R,9aS)-2-(5-fluoro-pyrimidin-2-yl)-2,3,4,6,7,8,9,9a-octahydro-1H-pyrido[1,2-a]pyrazin-7-ylmethyl]-3H-benzoxazol-2-one;

(7R,9aS)-7-(4-fluorophenoxy)methyl-2-(5-fluoro-pyrimiidin-2-yl)-2,3,4,6,7,8,9,9a-octahydro-1H-pyrido[1,2-a]pyrazine;

(7R,9aS)-7-(3,5-difluorophenoxy)methyl-2-(5-fluoro-pyrimidin-2-yl)-2,3,4,6,7,8,9,9a-octahydro-1H-pyrido[1,2-a]pyrazine;

(7R,9aS)-7-(3,4-difluorophenoxy)methyl-2-(5-fluoro-pyrimidin-2-yl)-2,3,4,6,7,8,9,9a-octahydro-1H-pyrido[1,2-a]pyrazine;

(7R,9aS)-7-(3-cyanophenoxy)methyl-2-(5-fluoro-pyrimidin-2-yl)-2,3,4,6,7,8,9,9a-octahydro-1H-pyrido[1,2-a]pyrazine;

(7R,9aS)-7-(4-cyanophenoxy)methyl-2-(5-fluoro-pyrimidin-2-yl)-2,3,4,6,7,8,9,9a-octahydro-1H-pyrido[1,2-a]pyrazine;

(7R,9aS)-7-(4-iodophenoxy)methyl-2-(5-fluoro-pyrimidin-2-yl)-2,3,4,6,7,8,9,9a-octahydro-1H-pyrido[1,2-a]pyrazine;

(7R,9aS)-7-(4-fluorophenoxy)methyl-2-(4-fluorophenyl)-2,3,4,6,7,8,9,9a-octahydro-1H-pyrido[1,2-a]pyrazine;

(7S,9aS)-7-(4-fluorophenoxy)methyl-2-(5-fluoro-pyrimidin-2-yl)-2,3,4,6,7,8,9,9 a-octahydro-1H-pyrido[1,2-a]pyrazine;

(7S,9aS)-7-(2-carbomethoxy-4-fluorophenoxy)methyl-2-(5-fluoro-pyrimidin-2-yl)-2,3,4,6,7,8,9,9a-octahydro-1H-pyrido[1,2-a]pyrazine;

(7S,9aS)-7-(2-bromo-4-fluorophenoxy)methyl-2-(5-fluoro-pyrimidin-2-yl)-2,3,4,6,7,8,9,9a-octahydro-1H-pyrido[1,2-a]pyrazine;

(7S,9aS)-7-(4-fluoro-2-trifluoromethylphenoxy)methyl-2-(5-fluoro-pyrimidin-2-yl)-2,3,4,6,7,8,9,9a-octahydro-1H-pyrido[1,2-a]pyrazine;

(7S,9aS)-7-(3,5-difluorophenoxy)methyl-2-(5-chloro-pyridin-2-yl)-2,3,4,6,7,8,9,9a-octahydro-1H-pyrido[1,2-appyrazine;

(7S,9aS)-7-(4-fluorophenoxy)methyl-2-(5-chloro-pyridin-2-yl)-2,3,4,6,7,8,9,9a-octahydro-1 H-pyrido[1,2-a]pyrazine;

(7S,9aS)-7-(2-chlorophenoxy)methyl-2-(5-fluoro-pyrimidin-2-yl)-2,3,4,6,7,8,9,9a-octahydro-1H-pyrido[1,2-a]pyrazine;

(7S,9aS)-7-(4-fluoro-2-methylphenoxy)methyl-2-(5-fluoro-pyrimidin-2-yl)-2,3,4,6,7,8,9,9a-octahydro-1H-pyrido[1,2-a]pyrazine;

(7S,9aS)-7-(2,4-difluorophenoxy)methyl-2-(5-fluoro-pyrimidin-2-yl)-2,3,4,6,7,8,9,9a-octahydro-1H-pyrido[1,2-a]pyrazine; and the pharmaceutically acceptable salt thereof.

Embodiments of Formula II

In preferred embodiments of the invention, compounds used in the practice of the invention include those of the formula II, wherein $R^1$ is bromine and $X^2$ is nitrogen; or wherein $R^1$ is chlorine and $X^2$ is nitrogen.

Examples of specific compounds based on formula II used in this invention include the following:

1-[3-(4-pyridin-2-yl-piperazin-1-yl)-propyl]-1,3-dihydro-benzoimidazol-2-one;

1-{3-[4-(5-trifluoromethyl-pyridin-2-yl)-piperazin-1-yl]-propyl}-1,3 -dihydro-benzoimidazol-2-one;

1-{3-[4-(5-chloro-pyridin-2-yl)-piperazin-1-yl]-propyl}-1,3 -dihydro-benzoimidazol-2-one;

1-{3-[4-(5-bromo-pyridin-2-yl)-piperazin-1-yl]-propyl}-1,3 -dihydro-benzoirnidazol-2-one;

1-[3-(2,3,5,6-tetrahydro-[1,2']bipyrazinyl-4-yl)-propyl]-1,3-dihydro-benzoimidazol-2-one; and 1-{3-[4-(6-chloro-pyridazin-3-yl)-piperazin-1-yl]-propyl}-1,3 -dihydro-benzoimidazol-2-one.

Other embodiments of this invention include methods using compounds of the formula II wherein $X^2$ is carbon, $X^3$ is nitrogen and $R^1$ is hydrogen or substituted or unsubstituted alkoxy; or wherein $X^2$ and $X^3$ are both carbon and $R^1$ is hydrogen or substituted or unsubstituted alkoxy; or wherein $X^1$ is carbon; or wherein $X^2$ and $X^3$ are both carbon and each of $R^0$, $R^1$ and $R^2$ is other than a fluoroalkyl group; or wherein $X^1$ is nitrogen.

Other embodiments of this invention include use of the following compounds of formula II:

1-[2-cyano-3-(2,3,5,6-tetrahydro-[1,2']bipyrazinyl-4-yl)-propyl]-1,3 -dihydro-benzoimidazol-2-one;

1-[5-methyl,3-(2,3,5,6-tetrahydro-[1,2']bipyrazinyl-4-yl)-propyl]-1,3 -dihydro-benzoimidazol-2-one;

1-[6-cyano,3-(2,3,5,6-tetrahydro-[1,2']bipyrazinyl-4-yl)-propyl]-1,3 -dihydro-benzoimidazol-2-one;

1-{[3-[4-(5-fluoro-pyridin-2-yl]-propyl]-3-methyl-1,3-methyl-1,3-dihydro-benzoimidazol-2-one;

1-{[3-[4-(3-cyano-pyridin-2-yl)-piperazin-1-yl]-propyl]-1,3-dihydro-benzoimidazol-2-one;

1-(3-[4-(4-cyano-pyridin-2-yl)-piperazin-1-yl]-propyl]-1,3-dihydro-benzoimidazol-2-one;

1-{3-[4-(6-trifluoromethyl-pyridin-2-yl)-piperazin-1-yl]-propyl}-1,3-dihydro-benzoimidazol-2-one;

1-{3-[4-(5-fluoro-pyridin-2-yl)-piperazin-1-yl]-propyl}-5-fluoro-1,3-dihydro-benzoimidazol-2-one; and 1-{3-[4-(5,fluoro-pyridin-2-yl)-piperazin-1-yl]-propyl}-5,6-difluoro-1,3-dihydro-benzoimidazol-2-one.

Preferred embodiments of the invention include a method of treating or preventing a novelty-seeking disorder, comprising administering to the subject an effective amount of any of the following compounds:

1-Benzoimidazol-1-yl-3-[4-(4-fluoro-phenyl)-piperazin-1-yl]-propan-2-ol;

1-(5-Chloro-benzoimidazol-1-yl)-3-[4-(4-fluoro-phenyl)-piperazin-1-yl]-propan-2-ol;

1-{3-[4-(4-Fluoro-phenyl)-piperazin-1-yl]-propyl}-5-trifluoromethyl-1H-benzoimidazole;

1-{3-[4-(4-Fluoro-phenyl)-piperazin-1-yl]-propyl}-1H-benzoimidazole;

1-{3-[4-(4-Fluoro-phenyl)-piperazin-1-yl]-propyl}-3-methyl-1,3-dihydro-benzoimidazol-2-one;

1-Benzoimidazol-1-yl-3-(4-o-tolyl-piperazine-1-yl)-propan-2-ol;

1-Benzoimidazol-1-yl-3-(4-m-tolyl-piperazine-1-yl)-propan-2-ol;

1-Benzoimidazol-1-yl-3-(4-p-tolyl-piperazine-1-yl)-propan-2-ol;

1-Benzoimidazol-1-yl-3-{4-chloro-phenyl)-phenyl-methyl]-piperazin-1-yl}-propan-2-ol;

1-Benzoimidazol-1-yl-3-[4-(2-chloro-phenyl)-piperazin-1-yl]-propan-2-ol;

1-Benzoimidazol-1-yl-3-[4-(4-chloro-phenyl)-piperazin-1-yl]-propan-2-ol;

1-Benzoimidazol-1-yl-3-[4-(3-chloro-phenyl)-piperazin-1-yl]-propan-2-ol;

1-Benzoimidazol-1-yl-3-[4-(3-chloro-phenyl)-piperazin-1-yl]-propan-2-ol;

1-Benzoimidazol-1-yl-3-(4-pyrimidin-2-yl-piperazin-1-yl)-propan-2-ol;

1-Benzoimidazol-1-yl-3-(4-naphthalen-1-yl-piperazin-1-yl)-propan-2-ol;

1-Benzoimidazol-1-yl-3-[4-(3-trifluoromethyl-phenyl)-piperazin-1-yl]-propan-2-ol;

1-Benzoimidazol-1-yl-3-(4-benzyl-piperazin-1-yl)-propan-2-ol;

1-Benzoimidazol-1-yl-3-[4-(2-trifluoromethyl-benzyl)-piperazin-1-yl]-propan-2-ol;

1-Benzoimidazol-1-yl-3-[4-(2-ethoxy-benzyl)-piperazin-1-yl]-propan-2-ol;

1-Benzoimidazol-1-yl-3-{4-{3-(3-trifluoromethyl-phenyl)-propyl]-piperazin-1-yl}-propan-2-ol; and 1-Benzoimidazol-1-yl-3-{4-[2-(3-trifluoromethyl-phenyl)-ethyl]-piperazin-1-yl}-propan-2-ol;

Other preferred embodiments of the invention include a method of treating or preventing a novelty-seeking disorder, comprising administering to the subject an effective amount of any of the following compounds of formula II:

(4-Chloro-2-nitro-phenyl)-{3-[4-(4-fluoro-phenyl)-piperazin-1-yl]-propyl}-amine;

{3-[4-(4-Fluoro-phenyl)-piperazin-1-yl]-propyl}-(2-nitro-4-trifluoromethyl-phenyl)-amine;

4-Chloro-N1-{3-[4-(4-fluoro-phenyl)-piperazin-1-yl}-propyl}-benzene-1,2-diamine;

1-(4,5-Dichloro-2-nitro-phenylamino)-3-[4-(4-fluoro-phenyl)-piperazin-1-yl]-propan-2-ol;

n1-[4-(4-Fluoro-phenyl)-piperazin-1-yl]-3-(2-phenyl-benzoimidazol-1-yl)-propan-2-ol;

1-[4-(4-Fluoro-phenyl)-piperazin-1-yl]-3-(2-propyl-benzoimidazol-1-yl)-propan-2-ol;

1-[4-(4-Fluoro-phenyl)-piperazin-1-yl]-3-(2-methyl-benzoimidazol-1-yl)-propan-2-ol;

5-Fluoro-1-(3-[4-(4-fluoro-phenyl)-piperazin-1-yl]-propyl)-2-methyl-1H-benzoimidazole;

5-Chloro-1-(3-[4-(4-fluoro-phenyl)-piperazin-1-yl]-2-hydroxy-propyl)-1,3-dihydro-benzoimidazol-2-one;

5-Fluoro-1-(3-[4-(4-fluoro-phenyl)-piperazin-1-yl]-2-hydroxy-propyl)-1,3-dihydro-benzoimidazol-2-one;

1-Benzoimidazol-1-yl-3-[4-(3-methoxy-phenyl)-piperazin-1-yl]-propan-2-ol;

1-Benzoimidazol-1-yl-3-[4-(4-methoxy-phenyl)-piperazin-1-yl]propan-2-ol;

1-Benzoimidazol-1-yl-3-(4-phenyl-piperazin-1-yl)-propan-2-ol;

1-{4-[4-(3-Benzoimidazol-1-yl-2-hydroxy-propyl)-piperazin-1-yl]-phenyl}-ethanone;

1-(4-Benzo[1,3]dioxol-5-ylmethyl-piperazin-1-yl)-3-benzoimidazol-1-yl-propan-2-ol;

1-Benzoimidazol-1-yl-3-[4-(3,4-dimethyl-phenyl)-piperazin-1-yl]-propan-2-ol;

4-[4-(3-Benzoimidazol-1-yl-2-hydroxy-propyl)-piperazin-1-yl]-phenol;

1-Benzoimidazol-1-yl-3-(4-phenethyl-piperazin-1-yl)-propan-2-ol;

1-Benzoimidazol-1-yl-3-[4-(3-phenyl-allyl)-piperazin-1-yl]propan-2-ol;

1-Benzoimidazol-1-yl-3-[4-(3-chloro-propyl)-piperazin-1-yl]-propan-2-ol;

2-[4-(3-Benzoimidazol-1-yl-2-hydroxy-propyl)-piperazin-1-yl-1-morpholin-4-yl-ethanone;

1-(4-Benzhydryl-piperazin-1-yl)-3-benzoimidazol-1-yl-propan-2-ol;

1-Benzoimidazol-1-yl-3-{4-[bis-(4-fluoro-phenyl)-methyl]-piperazin-1-yl}-propan-2-ol;

1-Benzoimidazol-1-yl-3-[4-(4-nitro-phenyl)-piperazin-1-yl]-propan-2-ol;

4-(3-Benzoimidazol-1-yl-2-hydroxy-propyl)-piperazine-1-carboxylic;

5-Fluoro-1-{3-[4-(4-fluoro-phenyl)-piperazin-1-yl]-propyl}-1H-benzoimidazole;

3-[4-(3-Benzoimidazol-1-yl-2-hydroxy-propyl)-piperazin-1-yl]-1-yl]-1-phenyl-propan-1-one;

4-[4-(3-Benzoimidazol-1-yl-2-hydroxy-propyl)-piperazin-1-yl]-1-(4-fluoro-phenyl)-butan-1-one;

1-Benzoimidazol-1-yl-3-[4-(tetrahydro-furan-2-ylmethyl)-piperazin-1-yl]-propan-2-ol;

[4-(3-Benzoimidazol-1-yl-2-hydroxy-propyl)-piperazin-1-yl]-(tetrahydro-furan-2-yl)-methanone;

[4-(3-Benzoimidazol-1-yl-2-hydroxy-propyl)-piperazin-1-yl]-(2,3-dihydro-benzo[1,4]dioxin-2-yl)-methanone;

[4-(3-Benzoimidazol-1-yl-2-hydroxy-propyl)-piperazin-1-yl]-(tetrahydro-furan-2-yl)-methanone;

[4-(3-Benzoimidazol-1-yl-2-hydroxy-propyl)-piperazin-1-yl]-2,3-dihydro-benzo[1,4]dioxin-2-yl)-methanone;

1-Benzoimidazol-1-yl-3-[4-(2,3-dihydro-benzo[1,4]dioxin-2-ylmethyl)-piperazin-1-yl]-propan-2-ol;

1-Benzoimidazol-1-yl-3-[4-2-nitro-butyl)-piperazin-1-yl]-propan-2-ol;

3-[4-(3-Benzoimidazol-1-yl-2-hydroxy-propyl)-piperazin-1-yl]-1-(4-chloro-phenyl)-propan-1-one;

1-Benzoimidazol-1-yl-3-[4-(5,5-diphenyl-pent-3-phenyl)-piperazin-1-yl]-propan-2-ol;

1-[4-(4-Fluoro-phenyl)-piperazin-1-yl]-3-(2-phenyl-benzoimidazol-1-yl)-propan-2-ol;

5,6-Difluoro-1-{3-[4-(4-fluoro-phenyl)-piperazin-1-yl]-propyl}-1H-benzoimidazol; and 1-[4-(4-Fluoro-phenyl)-piperazin-1-yl]-3-(2-propyl-benzoimidazol-1-yl)-propan-2-ol.

Embodiments of Formula III

Other embodiments of this invention include a method of treating or preventing a novelty-seeking disorder, comprising administering to the subject an effective amount of any of the following compounds:

(a) compounds of formula III wherein $R^1$ is phenyl and is either unsubstituted or substituted with one or two substituents selected from halo, $(C_1-C_6)$alkyl substituted with from one to three fluorine atoms, $(C_1-C_6)$ alkoxy substituted with from one to three fluorine atoms, cyano, —C(=O)$R^8$, aryl and heteroaryl;

(b) compounds of formula III wherein $R^1$ is indanyl and is either unsubstituted or substituted with one or two substituents selected from halo, $(C_1-C_6)$alkyl substituted with from one to three fluorine atoms, $(C_1-C_6)$ alkoxy substituted with from one to three fluorine atoms, cyano, —C(=O)$R^8$, aryl and heteroaryl;

(c) compounds of formula III wherein $R^1$ is naphthyl and is either unsubstituted or substituted with one or two substituents selected from halo, $(C_1-C_6)$alkyl substituted with from one to three fluorine atoms, $(C_1-C_6)$ alkoxy substituted with from one to three fluorine atoms, cyano, —C(=O)$R^8$, aryl and heteroaryl;

(d) compounds of formula III wherein $R^1$ is heteroaryl and is either unsubstituted or substituted with one or two substituents selected from halo, $(C_1-C_6)$alkyl substituted with from one to three fluorine atoms, $(C_1-C_6)$alkoxy substituted with from one to three fluorine atoms, cyano, —C(=O)$R^8$, aryl and heteroaryl;

(e) compounds of formula III wherein $R^5$, $R^6$ and $R^7$ are independently selected from $(C_1-C_6)$alkyl optionally substituted with from one to three fluorine atoms, $(C_1-C_6)$alkoxy optionally substituted with from one to three fluorine atoms, cyano and halo;

(f) compounds of formula III wherein $R^4$ is hydrogen;

(g) compounds of formula III wherein $R^4$ is $(C_1-C_6)$alkyl;

(h) compounds of formula III wherein $R^4$ is amino;

(i) compounds of formula III wherein $R^4$ is —$NHR^{10}$;

(j) compounds of formula III wherein $R^4$ is $SR^{10}$;

(k) compounds of formula III wherein $R^4$ is —$OR^{10}$;

(l) compounds of formula III wherein $R^4$ is hydroxy;

(m) compounds of formula III wherein $R^{11}$ is absent;

(n) compounds of formula III wherein $R^2$ and $R^3$ are both hydrogen;

(o) compounds of formula III wherein one or both of $R^2$ and $R^3$ are hydroxy;

(p) compounds of formula III wherein $R^2$ and $R^3$ together form an oxo group;

(q) compounds of formula III wherein one of $R^2$ and $R^3$ is $(C_1-C_6)$alkyl;

(r) compounds of formula III wherein X is carbon;

(s) compounds of formula III wherein X is nitrogen;

(t) compounds of formula III wherein $R^4$ is oxygen; and (v) compounds of formula III wherein $R^4$ is sulfur.

Emodiments of Formula IV

Certain embodiments of the invention include a method of treating or preventing a novelty-seeking disorder, comprising administering to the subject an effective amount of compounds of formula IV having the following structure

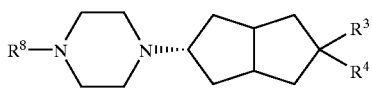

wherein $R^3$ is —(CH$_2$)$_t$(C$_6$–C$_{10}$ aryl) or —(CH$_2$)$_t$(4–10 membered heterocyclic), $R^4$ is H or hydroxy, and $R^8$ is —(CH$_2$)$_t$(C$_6$–C$_{10}$ aryl) or —(CH$_2$)$_t$(4–10 membered heterocyclic), t is an integer ranging from 0 to 5, and the foregoing $R^3$ and $R^8$ heterocyclic groups are optionally fused to a benzene ring, and said $R^3$ and $R^8$ groups are optionally substituted by 1 to 3 $R^{10}$ groups. More specific embodiments include use of those compounds wherein $R^8$ and $R^3$ are each independently selected from phenyl and pyrimidyl, optionally substituted by 1 to 3 substituents independently selected from halo, cyano, methoxy, trifluoromethyl, methanesulfonyl, amino, trifluoromethoxy, acetamido, and $C_1$–$C_6$ alkyl. Other more specific embodiments include those wherein $R^3$ is a heterocyclic group fused to a benzene ring and, optionally, 1 or 2 of the carbon atoms of said heterocyclic group is replaced with an oxo —C(O)— group. In particular, such specific embodiments of the invention use compounds wherein $R^3$ comprises the following groups:

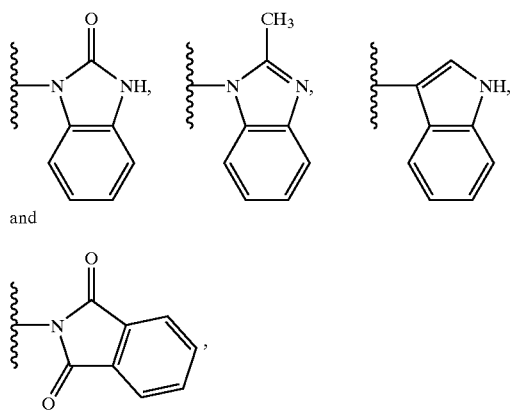

wherein the benzo portion of the above $R^3$ groups is optionally substituted by 1 to 3 $R^{10}$ groups Other embodiments of the invention include a method of treating or preventing a novelty-seeking disorder, comprising administering to the subject an effective amount of any compound of formula IV having the following structure

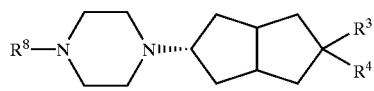

wherein $R^3$ is —O(CH$_2$)$_t$(C$_6$–C$_{10}$ aryl) or —O(CH$_2$)$_t$(4–10 membered heterocyclic), $R^4$ is H or hydroxy, and $R^8$ is —(CH$_2$)$_t$(C$_6$–C$_{10}$ aryl) or —(CH$_2$)$_t$(4–10 membered heterocyclic), wherein t is an integer ranging from 0 to 5, and wherein the foregoing $R^3$ and $R^8$ groups are optionally substituted by 1 to 3 $R^{10}$ groups. More specific embodiments of the invention include the described method wherein $R^3$ is phenoxy and $R^8$ is phenyl or pyrimidyl, and said $R^3$ and $R^8$ groups are optionally substituted by 1 to 3 substituents independently selected from halo, cyano, methoxy, trifluoromethyl, methanesulfonyl, amino, trifluoromethoxy, acetamido, and $C_1$–$C_6$ alkyl.

Other embodiments of the invention include a method of treating or preventing a novelty-seeking disorder, comprising administering to the subject an effective amount of any compound: of formula IV having the following structure

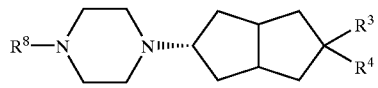

wherein $R^3$ and $R^4$ are taken together with the carbon atom to which each is attached to form a 5–10 membered monocyclic or bicyclic group wherein said cyclic group may be carbocyclic or heterocyclic with 1 to 3 heteroatoms selected from O, S, and —N($R^{11}$)— with the proviso that two O atoms, two S atoms, or an O and S atom are not attached directly to each other; said cyclic group is saturated or partially unsaturated; aromatic or non-aromatic; 1 or 2 of the carbon atoms in said cyclic group optionally may be replaced by an oxo —C(O)— moiety; and said cyclic group is optionally substituted by 1 to 3 $R^{10}$ groups; and $R^8$ is —(CH$_2$)$_t$(C$_6$–C$_{10}$ aryl) or —(CH$_2$)$_t$(4–10 membered heterocyclic), wherein t is an integer ranging from 0 to 5 and said $R^8$ group is optionally substituted by 1 to 3 $R^{10}$ groups. More specific embodiments of the invention include the described method wherein $R^8$ is phenyl or pyrimidyl, and $R^3$ and $R^4$ are taken together to form a group selected from and

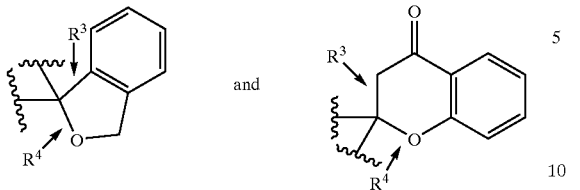

and said $R^8$, $R^3$ and $R^4$ groups are optionally substituted by 1 to 3 substituents independently selected from halo, cyano, methoxy, trifluoromethyl, methanesulfonyl, amino, trifluoromethoxy, acetamido, and $C_1$–$C_6$ alkyl.

Specific embodiments of the invention include a method of treating or preventing a novelty-seeking, comprising administering to the subject an effective amount of any of the following compounds of formula IV:

(2'α,3'aβ,5'α,6'aβ)-5'-[4-(4-Fluoro-phenyl)-piperazin-1-yl]-hexahydropentalene-2'-one;

(2'α,3'aβ,5'α,6'aβ)-5'-[4-(4-Fluoro-phenyl)-piperazin-1-yl]-2'-phenyl-octahydro-pentalen-2'ol, maleate salt;

(2'α,3'aβ,5'α,6'aβ)-5'-[4-(4-Cyano-3-fluoro-phenyl)-piperazin-1-yl]-hexahydropentalene-2-one, ethylene ketal;

(2'α,3'aβ,5'α,6'aβ)-5'-[4-(4-Cyano-3-fluoro-phenyl)-piperazin-1-yl]-hexahydropentalene-2-one;

(2'α,3'aβ,5'α,6'aβ)-2-Fluoro-4-[4-(5'-hydroxy-5'-phenyl-octahydro-pentalen-2'-yl)-pipeerazin-1-yl]-benzonitrile, maleate salt;

(2α,3aβ,5α,6aβ)-5-Hydroxy-5-phenyl-hexahydro-pentalen-2-one;

(2'α,3'aβ,5'α,6'aβ)-5'-[4-(2-Methoxy-phenyl)-piperazin-1-yl]-2'-phenyl-octahydro-pentalen-2'ol, maleate salt;

(2'α,3'aβ,5'α,6'aβ)-5'-[4-(4-Fluoro-1-pyrimidyl)-piperazin-1-yl]-2'-(4flouro-phenyl)-octahydro-pentalen-2'ol, maleate salt;

(2'α,3'aβ,5'α,6'aβ)-5'-[4-(4-Cyano-3-fluoro-phenyl)-piperazin-1-yl]-2'-(4-fluoro-phenyl)-octahydro-pentalen-2'ol, maleate salt;

(2'α,3'aβ,5'α,6'aβ)-5'-[4-(4-Fluoro-phenyl)-piperazin-1-yl]-2'-(4-fluoro-phenyl)-octahydro-pentalen-2'ol, maleate salt;

(2'α,3'aβ,6'aβ)-1-(4-Fluoro-phenyl)-4-(5'-phenyl-1',2',3',3'a,4',6'a-hexahydro-pentalen-2'-yl)-piperazine dihydrochloride;

(2'α,3'aβ,6'aβ)-5-Fluoro-2-[4-(5'-phenyl-1',2',3',3'a,4',6'a-hexahydro-pentalen-2'-yl)-piperazin-1-yl]-pyrimidine maleate;

(2'α,3'aβ,6'aβ)-2-Fluoro-4-[4-(5'-phenyl-1',2',3',3'a,4',6'a-hexahydro-pentalen-2'-yl)-piperazin-1-yl]-benzonitrile, maleate;

(2'α,3'aβ,6'aβ)-2-Fluoro-4-{4-[5-(2-methoxy-phenyl)-1',2',3',3'a,4',6'a-hexahydro-pentalen-2'-yl]-piperazin-1-yl}-benzonitrile, maleate;

(2'α,3'aβ,6'aβ)-1-Phenyl-4-(5'-phenyl-1',2',3',3'a,4',6'a-hexahydro-pentaleno-2'-yl)-piperazine, dimaleate;

(2'α,3'aβ,5'α,6'aβ)-1-(4-Fluoro-phenyl)-4-(5'-phenyl-octahydro-pentalen-2'-yl)-piperazine, dihydrochloride;

(2'α,3'aβ,5'α,6'aβ)-5-Fluoro-2-[4-(5'-phenyl-octahydro-pentalen-2'-yl)-piperazin-1-yl]-pyrimidine, maleate;

(2'α,3'aβ,5'α,6'aβ)-2-Fluoro-4-[4-(5'-phenyl-octahydro-pentalen-2'-yl)-piperazin-1-yl]-benzonitrile, maleate;

(2'α,3'aβ,5'α,6'aβ)-1-Phenyl-4-(5'-phenyl-octahydro-pentalen-2'-yl)-piperazine, maleate;

(2'α,3'aβ,5'α,6'aβ)-5'-Hydroxy-5'-(2-trifluoromethyl-phenyl)-hexahydro-pentalen-2'-one;

(2'α,3'aβ,6'aβ)-5'-(2-trifluoromethyl-phenyl)-3,3a,4,6a-tetrahydro-1H-pentalen-2'-one, ethylene ketal;

(2'α,3'aβ,5'α,6'aβ)-5'-(2-Trifluoromethyl-phenyl)-hexahydro-1H-pentalen-2'-one, ethylene ketal;

(2'α,3'aβ,5'α,6'aβ)-5'-(2-Trifluoromethyl-phenyl)-hexahydro-1H-pentalen-2'-one;

(2'α,3'aβ,5'α,6'aβ)-2-Fluoro-4-{4-[5'-(2-trifluoromethyl-phenyl)-octahydro-pentalen-2'-yl]-piperazin-1-yl}-benzonitrile, maleate;

(2'α,3'aβ,5'α,6'aβ)-2-Fluoro-4-{4-[5'-(2-methoxy-phenyl)-octahydro-pentalen-2'-yl]-piperazin-1-yl}-benzonitrile, maleate;

(2'α,3'aβ,5'α,6'aβ)-5-Fluoro-2-{4-[5'-(2-methoxy-phenyl)-octahydro-pentalen-2'-yl]-piperazin-1-yl}-pyrimidine, maleate;

(2'α,3'aβ,5'α,6'aβ)-2-Fluoro-4-{4-[5'-(3-methoxy-phenyl)-octahydro-pentalen-2'-yl]-piperazin-1-yl}-benzonitrile, maleate;

(2'α,3'aβ,5'α,6'aβ)-2-Fluoro-4-{4-[5'-(4-methoxy-phenyl)-octahydro-pentalen-2'-yl]-piperazin-1-yl}-benzonitrile, maleate;

(2'α,3'aβ,5'α,6'aβ)-2-Fluoro-4-[4-(5'-o-tolyl-octahydro-pentalen-2'-yl)-piperazin-1-yl]-benzonitrile, maleate;

(2'α,3'aβ,5'α,6'aβ)-5-Fluoro-2-[4-(5'-o-tolyl-octahydro-pentalen-2'-yl)-piperazin-1-yl]-pyrimidine, maleate;

(2'α,3'aβ,5'α,6'aβ)-5-Chloro-2-{4-[5'-(2-methoxy-phenyl)-octahydro-pentalen-2'-yl]-piperazin-1-yl}-pyrimidine, maleate;

(2'α,3'aβ,5'α,6'aβ)-5-Chloro-2-[4-(5'-o-tolyl-octahydro-pentalen-2'-yl)-piperazin-1-yl]-pyrimidine, maleate;

(2'α,3'aβ,5'α,6'aβ)-2-Fluoro-4-{4-[5'-(2-methanesulfonyl-phenyl)-octahydro-pentalen-2'-yl]-piperazin-1-yl}-benzonitrile, maleate;

(2'α,3'aβ,5'α,6'aβ)-1-Phenyl-4-[5'-(3-pyrrolidin-1-ylmethyl-phenyl)-octahydro-pentalen-2'-yl]-piperazine, dimaleate;

5-Trimethylstannayl-3,3a,4,6a-tetrahydro-1H-pentalen-2-one, ethylene ketal;

5-(2-Cyano-phenyl)-3,3a,4,6a-tetrahydro-1H-pentalen-2-one;

(2'α,3'aβ,5'α,6'aβ)-2-Cyano-4-{4-[5'-(2-fluoro-phenyl)-octahydro-pentalen-2'-yl]-piperazin-1-yl}-benzonitrile, maleate;

(2'α,3'aβ,5'α,6'aβ)-2-Fluoro-4-{4-[5'-(2-trifluoromethoxy-phenyl)-octahydro-pentalen-2'-yl]-piperazin-1-yl}-benzonitrile, maleate;

(2'α,3'aβ,5'α,6'aβ)-2-Fluoro-4-{4-[5'-(2-fluoro-phenyl)-octahydro-pentalen-2'-yl]-piperazin-1-yl}-benzonitrile, maleate;

(2'α,3'aβ,5'α,6'aβ)-2-Fluoro-4-[4-(5'-pyridin-2-yl-octahydro-pentalen-2'-piperazin-1-yl]-benzonitrile, dihydrochloride;

(2'α,3'aβ,5'α,6'aβ)-2-Fluoro-4-[4-(5'-m-tolyl-octahydro-pentalen-2'-yl)-piperazin-1-yl]-benzonitrile, maleate;

(2'α,3'aβ,5'α,6'aβ)-2-Fluoro-4-[4-(5'-p-tolyl-octahydro-pentalen-2'-yl)-piperazin-1-yl]-benzonitrile, maleate;

(2'α,3'aβ,5'α,6'aβ)-N-(2-{5'-[4-(5-Fluoro-pyrimidin-2-yl)-piperazin-1-yl]-octahydro-pentalen-2'-yl}-phenyl)-acetamide, maleate;

(2'α,3'aβ,5'α,6'aβ)-N-(2-{5'-[4-(4-Cyano-3-fluoro-phenyl)-piperazin-1yl]-octahydro-pentalen-2'-yl}-phenyl)-acetamide, maleate;

5-(2-Cyano-phenyl)-3,3a,4,6a-tetrahydro-1H-pentalen-2-one, ethylene ketal;

2-(5-Oxo-octahydro-pentalen-2-yl)-benzamide, ethylene ketal;

(2'α,3'aβ,5'α,6'aβ)-2-{5'-[4-(4-Cyano-3-fluoro-phenyl)-piperazin-1-yl]-octahydro-pentalen-2'-yl}-benzamide, maleate;

(2'α,3'aβ,5'α,6'aβ)-2-Fluoro-4-[4-(3',3'a,4',5',6',6'a-hexaydrospiro[isobenzofuran-1(3H),2'(1'H)-pentalen]-5'-yl)-1-piperazinyl]-benzonitrile, maleate;

(2'α,3'aβ,5'β,6'aβ)-2-Fluoro-4-[4-(3',3'a, 4',5',6',6'a-hexahydrospiro[isobenzofuran-1(3H),2'(1'H)-pentalen]-5'-yl)-1-piperazinyl]-benzo-nitrile, maleate;

(2'α,3'aβ,5'α,6'aβ)-5-Fluoro-2-[4-(3',3'a, 4',5',6',6'a-hexahydrospiro[isobenzofuran-1(3H),2'(1'H)-pentalen]-5'-yl)-piperazin-1-yl]-pyrimidine;

(2'α,3'aβ,5'α,6'aβ)-5-Fluoro-2-[4-(3',3'a, 4',5',6',6'a-hexahydrospiro[isobenzofuran-1(3H),2'(1'H)-pentalen]-5'-yl)-piperazin-1-yl]-pyrim-idine;

(2'α,3'aβ,5'α,6'aβ)-5-Fluoro-2-[4-(3',3'a, 4',5',6',6'a-dimethylspiro[isobenzofuran-1(3H), 2'(1'H)-pentalen]-5'-yl)-1-piperazinyl]-pyrimidine, maleate;

(2'α,3'aβ,5'α,6'aβ)-5-Fluoro-2-[4-(3',3'a, 4',5',6,6a-hexahydro-3'a,6'a-dimethylspiro[isobenzofuran-1(3H), 2'(1'H)-pentalen]-5'-yl)-1-piperazinyl]-pyrimidine, maleate;

(2'α,3'aβ,5'β,6'aβ)-2-Fluoro-4-[4-(3,3',3'a, 4,4',5',6',6'a-hexahydrospiro[2H-1-benzopyran-2,2'(1'H)-pentalen]-5'-yl)-1-piperazinyl]-benzonitrile, maleate;

(2'α,3'aβ,5'α,6'aβ)-2-Fluoro-4-[4-(3,3',3'a, 4,4',5',6',6'a-hexahydrospiro[2H-1-benzopyran-2,2'(1'H)-pentalen]-5'-yl)-1-piperazinyl]-benzonitrile, maleate;

(2'α,3'aβ,5'α,6'aβ)-1-Phenyl-4-(3,3',3'a, 4,4',5',6',6'a-hexahydrospiro[2H-1-benzopyran-2,2'(1'H)-pentalen]-5'-yl]-5'-yl)-piperazine, maleate;

(2'α,3'aβ,5'α,6'aβ)-1-Phenyl-4-(3,3',3'a, 4,4',5',6',6'a-hexahydrospiro[2H-1-benzopyran-2,2'(1'H)-pentalen]-5'-yl]-5'-yl)-piperazine, maleate;

(2'α,3'aβ,5'α,6'aβ)-2-Fluoro-4-[4-(3,3',3'a, 4,4',5',6',6'a-hexahydrospiro[2H-6-fluoro-1-benzopyran-2,2'(1'H)-pentalen]-5'-yl]-5'-yl)-1-piperazinyl]-benzonitrile, maleate;

(2'α,3'aβ,5'α,6'aβ)-2-Fluoro-4-[4-(3,3',3'a, 4,4',5',6',6'a-hexahydrospiro[2H-6-fluoro-1-benzopyran-2,2'(1'H)-pentalen]-5'-yl]-5'-yl)-1-piperazinyl]-benzonitrile, maleate;

(2'α,3'aβ,5'α,6'aβ)-5-Benzylamino-hexahydropentalen-2-one, mono-ethylene ketal;

(2'α,3'aβ,5'α,6'aβ)-5-Amino-hexahydropentalen-2-one, mono-ethylene ketal;

(2'α,3'aβ,5'α,6'aβ)-5-(5-Fluoro-2-nitro-phenylamino)-hexahydropentalen-2-one, mono-ethylene ketal;

(2'α,3'aβ,5'α,6'aβ)-5-(2-Amino-5-fluoro-phenylamino)-hexahydropentalen-2-one, mono-ethylene ketal;

(2'α,3'aβ,5'α,6'aβ)-2-Fluoro-4-{4-[5'-(6-fluoro-2-oxo-2,3-dihydro-benzoimidazol-1-yl)-octahydro-pentalen-2'-yl]-piperazin-1-yl}-benzonitrile, dimesylate;

(2'α,3'aβ,5'α,6'aβ)-2-Fluoro-4-{4-[5'-(2-oxo-2,3-dihydro-benzoimidazol-1-yl)-octahydro-pentalen-2'-yl]-piperazin-1-yl}-benzonitrile, mesylate;

(2'α,3'aβ,5'α,6'aβ)-1-{5'-[4-(5-Fluoro-pyrimidin-2-yl)-piperazin-1-yl]-octahydro-pentalen-2'-yl}-1,3-dihydro-benzoimidazol-2-one, mesylate;

(2'α,3'aβ,5'α,6'aβ)-5-(6-Fluoro-2-methyl-benzoimidazol-1-yl)-hexahydro-pentalen-2-one;

(2'α,3'aβ,5'α,6'aβ)-2-Fluoro-4-{4-[5'-(6-fluoro-2-methylbenzoimidazol-1-yl)-octahydro-pentalen-2'-yl]-piperazin-1-yl}-benzonitrile, dimesylate;

(2'α,3'aβ,5'α,6'aβ)-6-Fluoro-2-methyl-1-[5'-(4-phenyl-piperazin-1-yl)-octahydro-pentalen-2'-yl]-1H-benzoimidazole, dimaleate;

(2'α,3'aβ,6'aβ)-5-(1H-Indol-3-yl)-3,3a,4,6a-tetrahydro-1H-pentalen-2-one, mono-ethylene ketal;

(2'α,3'aβ,5'α,6'aβ)-2-Fluoro-4-{4-[5'-(1H-indol-3-yl)-octahydro-pentalen-2'-yl]-piperazin-1-yl}-benzonitrile, maleate;

(2'α,3'aβ,5'α,6'aβ)-3-[5'-(4-Phenyl-piperazin-1-yl)-octahydro-pentalen-2'-yl]1H-indole, maleate;

(2'α,3'aβ,5'α,6'aβ)-5-(4-Fluoro-phenoxy)-hexahydro-pentalen-2-one;

(2'α,3'aβ,5'β,6'aβ)-1-[5'-(4-Fluoro-phenoxy)-octahydro-pentalen-2'-yl]-4-phenyl-piperazine, maleate;

(2'α,3'aβ,5'β,6'aβ)-2-Fluoro-4-{4-[5'-(4-fluoro-phenoxy)-octahydro-pentalen-2'-yl]-piperazin-1-yl}-benzonitrile, maleate;

(2'α,3'aβ,5'β,6'aβ)-5-Fluoro-2-{4-[5'-(4-fluoro-phenoxy)-octahydro-pentalen-2'-yl]-piperazin-1-yl}-pyrimidine, maleate;

(2'α,3'aβ,5'β,6'aβ)-1-[5'-(4-Fluoro-phenoxy)-octahydro-pentalen-2'-yl]-4-phenyl-piperazine, maleate;

(2'α,3'aβ,5'β,6'aβ)-2-[5'-(4-Phenyl-piperazin-1-yl)-octahydro-pentalen-2'-yl]-isoindole-1,3-dione maleate;

(2'α,3'aβ,5'α,6'aβ)-5-Hydroxy-hexahydro-pentalen-2-one, ethylene ketal;

(2'α,3'aβ,5'α,6'aβ)-2-Oxo-3-(5-oxo-octahydro-pentalen-2-yl)-2,3-dihydro-benzoimidazole-1-carboxylic acid tert-butyl ester, ethylene ketal;

(2'α,3'aβ,5'α,6'aβ)-2-(5-oxo-octahydro-pentalen-2-yloxy)-3H-benzoimidazole-1-carboxylic acid tert-butyl ester, ethylene ketal;

(2'α,3'aβ,5'α,6'aβ)-3-{5'-[4-(4-Fluoro-phenyl)-piperazin-1-yl]-octahydro-pentalen-2'-yl}-2-oxo-2,3-dihydro-benzoimidazole-1-carboxylic acid tert-butyl ester;

(2'α,3'aβ,5'α,6'aβ)-1-{5'-[4-(4-Fluoro-phenyl)-piperazin-1-yl]-octahydro-pentalen-2'-yl}-1,3-dihydro-benzoimidazol-2-one, maleate;

(2'α,3'aβ,5'β,6'aβ)-2-Fluoro-4-{4-[5'-(2-oxo-2,3-dihydro-benzoimidazol-1-yl)-octahydro-pentalen-2'-yl]-piperazin-1-yl}-benzonitrile, maleate;

(2'α,3'aβ,5'α,6'aβ)-1-{5'-[4-(3,4-Difluoro-phenyl)-piperazin-1-yl]-octahydro-pentalen-2'-yl}-1,3-dihydro-benzoimidazol-2-one, maleate;

(2'α,3'aβ,5'α,6'aβ)-2-[5'-(4-Phenyl-piperazin-1-yl)-octahydro-pentalen-2'-yloxy]-1H-benzoimidazole, maleate;

(2'α,3'aβ,5'α,6'aβ)-2-(5-Oxo-octahydro-pentalen-2-yl)-isoindole-1,3-dione;

(2'α,3'aβ,5'β,6'aβ)-2-[5'-(4-Phenyl-piperazin-1-yl)-octahydro-pentalen-2'-isoindole-1,3-dione, maleate;

(2'α,3'aβ,5'β,6'aβ)-4-{4-[5'-(1,3-Dioxo-1,3-dihydro-isoindol-2-yl)-octahydro-pentalen-2'-yl]-piperazin-1-yl}-2-fluoro-benzonitrile, maleate;

(2'α,3'aβ,5'β,6'aβ)-2-{5'-[4-(5-Fluoro-pyrimidin-2-yl)-piperazin-1-yl]-octahydro-pentalen-2'-yl}-isoindole-1,3-dione, maleate;

(2'α,3'aβ,5'α,6'aβ)-2-{5'-[4-(3,4-Difluoro-phenyl)-piperazin-1-yl]-octahydro-pentalen-2'-yl}-isoindole-1,3-dione, maleate;

(2'α,3'aβ,5'α,6'aβ)-2-{5'-[4-(4-Fluoro-phenyl)-piperazin-1-yl]-octahydro-pentalen-2'-yl}-isoindole-1,3-dione, maleate; and, (2'α,3'aβ,5'α,6'aβ)-N-[5-(4-Phenyl-piperazin-1-yl)-octahydro-pentalen-2-yl]-benzamide, maleate.

Embodiments of Formula V

Preferred embodiments of the invention include a method of treating or preventing a novelty-seeking disorder, comprising administering to the subject an effective amount of the compound of formula V wherein X is nitrogen; or wherein Y and Z are each $CR^{12}$ wherein $R^{12}$ is hydrogen or fluoro; or wherein $R^2$ is hydrogen, fluoro or chloro; or wherein $R^3$, $R^4$ and $R^5$ are hydrogen; or wherein $R^7$ is fluoro or chloro; or wherein $R^9$ is fluoro, chloro, bromo or alkoxy; or, more specifically, wherein X is nitrogen; Y and Z are each $CR^{13}$ wherein $R^{13}$ is hydrogen or fluoro; $R^2$ is hydrogen fluoro or chloro; $R^3$, $R^4$ and $R^5$ are hydrogen; $R^7$ is fluoro or chloro; and $R^9$ is fluoro, chloro, bromo or alkoxy.

Specific preferred embodiments of the invention include a method of treating or preventing a novelty-seeking disorder, comprising administering to the subject an effective amount of any of the following compounds of formula V:

2-[4-(3-Trifluoromethyl-phenyl)-piperazin-1-ylmethyl]-1H-indole;

5-Fluoro-2-[4-(3-trifluoromethyl-phenyl)-piperazin-1-ylmethyl]-1H-indole;

5-Fluoro-2-[4-(4-fluoro-phenyl)-piperazin 1-ylmethyl]-1H-indole;

5-Fluoro-2-[4-(4-fluoro-phenyl)-piperazin-1-ylmethyl]-1H-indole;

5-Fluoro-2-(4-pyridin-2-yl-piperazin-1-ylmethyl)-1H-indole;

2-[4-(6-Chloro-pyridazin-3-yl)-piperazin-1-ylmethyl]-5-fluoro-1H-indole;

5-Fluoro-2-(4-[5'-fluoro]pyridin-2-yl-piperazin-1-ylmethyl)-1H-indole;

2-(4-pyridin-2-yl-piperazin-1-ylmethyl)-1H-azaindole;

5-Fluoro-2-(4-pyridin-2-yl-piperazin-1-ylmethyl)-1H-azaindole; and

2-[4-(4-fluoro-phenyl)-piperazin-1-ylmethyl]-1H-azaindole.

Embodiments of Formula VI

Preferred embodiments of the invention include a method of treating or preventing a novelty-seeking disorder, comprising administering to the subject an effective amount of any of the compounds of formula VI wherein a is oxygen, b is $CH_2$, each of $R^1$, $R^4$ and $R^5$ is hydrogen, and each of $R^2$, $R^3$ and $R^6$ is selected, independently from hydrogen, cyano, chloro and fluoro.

Other more specific embodiments of this invention include a method of treating or preventing a novelty-seeking disorder, comprising administering to the subject an effective amount of any of the following compounds:

(a) compounds of formula VI wherein a is oxygen;

(b) compounds of formula VI wherein a is oxygen and b is $CH_2$;

(c) compounds of formula VI wherein a is oxygen, b is $CH_2$ and each of $R^1$, $R^4$ and $R^5$ is hydrogen;

(d) compounds of formula VI wherein a is oxygen, b is $CH_2$, each of $R^1$, $R^4$ and $R^5$ is hydrogen and $R^3$ is fluoro, cyano or chloro;

(e) compounds of formula VI wherein a is oxygen, b is $CH_2$, each of $R^1$, $R^4$ and $R^5$ is hydrogen and each of $R^2$, $R^3$ and $R^6$ is selected, independently, from hydrogen, fluoro, cyano and chloro; and (f) compounds of formula VI wherein a is oxygen, b is $CH_2$, each of $R^1$, $R^4$ and $R^5$ is hydrogen, and $R^2$ and $R^3$ are selected, independently, from fluoro, cyano and chloro.

The compounds of formula I, II, III, IV, V and VI above may contain chiral centers and therefore may exist in different enantiomeric forms. This invention relates to a method of treating or preventing a novelty-seeking disorder, comprising administering to the subject an effective amount of any of the optical isomers and all other stereoisomers of compounds of the formula I, II, III, IV, V and VI and mixtures thereof.

The compounds of formula I, II, III, IV, V and VI that are basic in nature are capable of forming a wide variety of salts with various inorganic and organic acids. The acids that may be used to prepare pharmaceutically acceptable acid addition salts are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts.

Although such salts must be pharmaceutically acceptable for administration to animals, it is often desirable in practice to initially isolate a compound of the formula I, II, III, IV, V and VI from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the basic compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

The novel compounds of the formula I, II, III, IV, V and VI and the pharmaceutically acceptable salts thereof (herein referred to as "the therapeutic compounds of this invention") are useful as dopamine D4 receptor ligands, i.e., they possess the ability to inhibit the binding of dopamine D4 ligands to the dopamine D4 receptor in various subjects, including humans. They and other dopamine D4 receptor ligands are therefore able to function as therapeutic agents in the treatment or prevention of a variety of conditions in subjects, including humans, the treatment or prevention of which can be effected or facilitated by a decrease in binding of dopamine D4 receptor ligands with the dopamine D4 receptor, including a novelty-seeking disorder selected from pathological gambling, attention deficit disorder with hyperactivity disorder (ADHD), substance addiction (e.g., drug addiction and alcohol addiction) and sex addiction.

The term "dopaminergic effective amount", as used herein, refers to an amount sufficient to inhibit the binding of dopamine to a dopamine receptor.

The term "altering dopamine mediated neurotransmission", as used herein, includes but is not limited to increasing or decreasing D4 dopamine receptor mediated neurotransmission.

The term "novelty seeking disorder", as used herein, refers to a maladaptive variant of the personality trait of seeking novelty in the dimensional model of personality disorders. See DSM-IV. Examples of novelty-seeking disorders include: pathological gambling, attention deficit disorder with hyperactivity disorder (ADHD), substance addiction (e.g., drug addiction and alcohol addiction) and sex addiction.

DETAILED DESCRIPTION OF THE INVENTION

The compounds of the formula I, II, III, IV, V and VI may be prepared as described below. Unless otherwise indicated in the discussion that follows, structural formulae I, II, III, IV and V are defined as above.

Compounds of the formula I may be prepared as decribed in U.S. Pat. No. 5,852,031, issued Dec. 22, 1998. This patent is incorporated herein by reference in its entirety.

Compounds of the formula II may be prepared as described in U.S. Pat. No. 5,883,094, issued Mar. 16, 1999. This patent is incorporated herein by reference in its entirety.

Compounds of the formula III may be prepared as described in U.S. Pat. No. 5,889,010, issued Mar. 30, 1999. This patent is incorporated herein by reference in its entirety.

Compounds of the formula IV may be prepared as described in U.S. patent application Ser. No. 09/300,262, filed Apr. 27, 1999. This application is incorporated herein by reference in its entirety.

Compounds of the formula V may be prepared as described in PCT International Application No. PCT/IB98/01198 and designates the United States, and was published as Publication No. published as WO99/09025 on Feb. 25, 1999. This application is incorporated herein by reference in its entirety.

Compounds of the formula VI may be prepared as described in PCT International Application No. PCT/IB97/00978, which was filed in the International Bureau on Aug. 8, 1997 and designates the United States, and was published as Publication No. WO98/08835 on Mar. 5, 1998. This application is incorporated herein by reference in its entirety.

The compounds of the formula I, II, III, IV, V and VI, herein referenced to collectively as the "therapeutic agents" and the pharmaceutically acceptable salts thereof, are useful as dopamine D4 receptor ligands. Other dopamine D4 receptor ligands that may be used in accordance with the methods of this invention are the compounds and pharmaceutically acceptable salts thereof described in the following references: U.S. patent application Ser. No. 5,877,317 issued on Mar. 2, 1999; U.S. patent application Ser. No. 5,021,420, issued on Jun. 4, 1991; U.S. patent application Ser. No. 5,633,376, issued on May 27, 1997; U.S. patent application, Ser. No. 5,432,177, issued on Nov. 9, 1994; U.S. patent application Ser. No. 5,622,950, issued on Apr. 22, 1997, PCT International Application No. PCT/EP93/01438, published as WO94/00458 on Jan. 6, 1994; U.S. patent application Ser. No. 5,998,414, issued on Dec. 7, 1999; U.S. patent application Ser. No. 5,968,478, issued on Oct. 19, 1999; U.S. patent application Ser. No. 6,040,448, issued on Mar. 21, 2000; U.S. patent application Ser. No. 6,051,605, issued on Apr. 18, 2000; U.S. patent application Ser. No. 5,945,421, issued on Aug. 31, 1999; and U.S. patent application Ser. No. 5,798,350, issued on Aug. 25, 1998. Each of the foregoing patents and patent publications is incorporated herein by reference in its entirety.

The therapeutic compounds used in this invention can be administered orally, transdermally (e.g., through the use of a patch), parenterally or topically. Oral administration is preferred. In general, these compounds are most desirably administered in dosages ranging from about 0.1 mg up to about 1000 mg per day, or 1 mg to 1000 mg per day in some cases, although variations may occur depending on the weight and condition of the person being treated and the particular route of administration chosen. In some instances, dosage levels below the lower limit of the aforesaid range may be more than adequate, while in other cases still larger doses may be employed without causing any harmful side effect, provided that such larger doses are first divided into several small doses for administration throughout the day.

The therapeutic compounds used in the invention may be administered alone or in combination with pharmaceutically acceptable carriers or diluents by either of the two routes previously indicated, and such administration may be carried out in single or multiple doses. More particularly, the novel therapeutic compounds of this invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, elixirs, syrups, and the like. Such carriers include solid diluents or fillers, sterile aqueous media and various non-toxic organic solvents, for example. Moreover, oral pharmaceutical compositions can be suitably sweetened and/or flavored.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tableting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a therapeutic compound used in the present invention in either sesame or peanut oil or in aqueous propylene glycol may be employed. The aqueous solutions should be suitably buffered if necessary and the liquid diluent first rendered isotonic. These aqueous solutions are suitable for intravenous injection purposes. The oily solutions are suitable for intra-articular, intramuscular and subcutaneous injection purposes. The preparation of all these solutions under sterile conditions is readily accomplished by standard pharmaceutical techniques well known to those skilled in the art.

Additionally, it is also possible to administer the compounds used in the present invention topically when treating inflammatory conditions of the skin and this may preferably be done by way of creams, jellies, gels, pastes, ointments and the like, in accordance with standard pharmaceutical practice.

Dopaminergic activity of the compounds used in the invention is related to the ability of the compounds to bind to the $D_4$ receptors, and the relative ability of compounds of this invention to inhibit [$^3$H]-spiperone binding to human dopamine $D_4$ receptor subtypes expressed in clonal cell lines was measured using the following procedure.

The determination of $D_4$ receptor binding ability has been described by Van Tol et al., *Nature,* 350, 610 (1991)). Clonal cell lines expressing the human dopamine $D_4$ receptor are harvested and homogenized (polytron) in a 50 mM Tris:HCl (pH 7.4 at 4° C.) buffer containing 5 mM EDTA, 1.5 mM calcium chloride ($CaCl_2$), 5 mM magnesium chloride ($MgCl_2$), 5 mM potassium chloride (KCl) and 120 mM sodium chloride (NaCl). The homogenates are centrifugated for 10–15 min. at 48,000 g, and the resulting pellets resuspended in a buffer at a concentration of 150–250 mg/ml. For saturation experiments, 0.75 ml aliquots of tissue homogenate are incubated in triplicate with increasing concentrations of [$^3$H] spiperone (70.3 Ci/mmol; 10–3000 pM final concentration) for 30–120 minutes at 22° C. in a total volume of 1 ml. For competition binding experiments, assays are initiated by the addition of 0.75 ml of membrane and incubated in duplicate with the indicated concentrations of competing ligands ($10^{-14}$–$10^{-3}$ M) and/or [$^3$H]spiperone (100–300 pM) for 60–120 min at 22° C. Assays are terminated by rapid filtration through a Brandell cell harvester and the filters subsequently monitored for tritium as described by Sunahara, R. K. et al., *Nature,* 346, 76–80 (1990). For all experiments, specific [$^3$H]spiperone binding is defined as that inhibited by 1–10 mM (+)-butaclamol. Binding data are analyzed by non-linear least squares curve-fitting. All of the compounds recited herein which were tested in this assay were found to have binding affinities ($K_i$) for the displacement of [$^3$H]-spiperone of less than 2 micromolar.

Utility of the present invention may be determined for the recited dopamine D4 ligands by administering any of the ligands to subjects deemed to be suffering from a novelty-seeking disorder as determined from a Temperament and Character Inventory (Cloninger et al, *Arch. Gen. Psychiatry,* 50, 975–990 (1993)) and comparing the Novelty Seeking scores prior to and after the administration of the ligand. (See Malhotra et al., *Mol. Psychiatry,* 1, 388–391 (1996)). An improved Novelty Seeking score indicates an effective ligand dosage for administration to a subject in need of treatment.

What is claimed is:

1. A method of treating or preventing a novelty-seeking disorder in a subject in need thereof, said novelty-seeking disorder selected from pathological gambling, attention deficit disorder with hyperactivity disorder, and sex addition$_1$ comprising administering to the subject:

an amount of a compound having the formula:

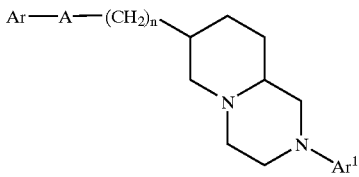

wherein Ar is phenyl, naphthyl, benzoxazolonyl, indolyl, indolonyl, benzimidazolyl, quinolyl, furyl, benzofuryl, thienyl, benzothienyl, oxazolyl, benzoxazolyl;

$Ar^1$ is phenyl, pyridinyl, pyridazinyl, pyrimidinyl, pyrazinyl, benzisoxazolyl, or benzisothiazolyl;

A is O, S, SO, $SO_2$, C=O, CHOH, or —($CR^3R^4$)—;

n is 0, 1 or 2;

each of Ar and $Ar^1$ may be independently and optionally substituted with one to four substituents independently selected from the groups consisting of fluoro, chloro, bromo, iodo, cyano, nitro, thiocyano, —SR, —SOR, —$SO^2R$, —$NHSO_2R$, —($C_1$–$C_6$)alkoxy, —$NR^1R^2$, —$NRCOR^1$, —$CONR^1R^2$, Ph, —COR, COOR, —($C_1$–$C_6$)alkyl, —($C_1$–$C_6$)alkyl substituted with one to six halogens, —($C_3$–$C_6$)cycloalkyl, and trifluoromethoxy;

each and every R, $R^1$, and $R^2$ is independently selected from the group consisting of hydrogen, —($C_1$–$C_6$) alkyl, —($C_1$–$C_6$)alkyl substituted with one to thirteen halogens selected from fluorine, chlorine, bromine and iodine, phenyl, benzyl, —($C_2$–$C_6$)alkenyl, —($C_3$–$C_6$) cycloalkyl, and , —($C_1$–$C_6$)alkoxy;

each and every $R^3$ and $R^4$ is independently selected from a group consisting of hydrogen, methyl, ethyl, n-propyl, and i-propyl;

diastereomeric and optical isomers thereof; and pharmaceutically acceptable salts thereof.

2. The method of claim 1, wherein the compound is selected from:

(7R,9aS)-7-(4-fluorophenoxy)methyl-2-(5-fluoropyrimidin-2-yl)-2,3,4,6,7,8,9,9a-octahydro-1H-pyrido[1,2-a]pyrazine;

(7R,9aS)-7-(3,4-difluorophenoxy)-methyl-2-(5-fluoropyrimidin-2-yl)-2,3,4,6,7,8,9,9a-octahydro-1H-pyrido[1,2-a]pyrazine;

(7R,9aS)-7-(4-fluorophenoxy)methyl-2-(5-chloropyridin-2-yl)-2,3,4,6,7,8,9,9a-octahydro-1H-pyrido[1,2-a]pyrazine;

2-(5-fluoropyrimidin-2-yl)-2,3,4,6,7,8,9,9a-octahydro-1H-pyrido[1,2a]-pyrazin-7-ylmethyl]-3H-benzoxazol-2-one hydrochloride;

3-[(7R,9aS)-2-(5-chloropyridin-2-yl)-2,3,4,6,7,8,9,9a-octahydro-1H-pyrido[1,2-a]pyrazin-7-ylmethyl]-3H-benzoxazol-2-one;

((7S,9aS)-7-(3-cyanophenoxy)methyl-2-(5-fluoropyrimidin-2-yl)-2,3,4,6,7,8,9,9a-octahydro-1H-pyrido [1,2-a]pyrazine.

3. A method of treating or preventing a novelty-seeking disorder in a subject in need thereof, said novelty-seeking disorder selected from pathological gambling, attention deficit disorder with hyperactivity disorder, and sex addition, comprising administering to the subject an amount of a dopamine D4 receptor ligand, or a pharmaceutically acceptable salt thereof, effective to treat or prevent a novelty-seeking disorder in the subject.

* * * * *